United States Patent [19]

Kawasaki et al.

[11] Patent Number: 4,839,283

[45] Date of Patent: Jun. 13, 1989

[54] METHOD OF EXPRESSING ALPHA-1-ANTITRYPSIN IN YEAST

[75] Inventors: Glenn H. Kawasaki; Richard Woodbury, both of Seattle, Wash.

[73] Assignee: ZymoGenetics, Inc., Seattle, Wash.

[21] Appl. No.: 946,640

[22] Filed: Dec. 30, 1986

[51] Int. Cl.$^4$ .................. C12N 5/00; C12N 15/00; C12P 21/00

[52] U.S. Cl. .................................. 435/68; 435/70; 435/172.3; 435/255; 435/256; 435/320; 435/172.1; 536/27; 935/28; 935/37; 935/56; 935/69

[58] Field of Search ............... 435/68, 255, 172.3, 435/317, 320; 536/27; 424/94; 530/350; 935/28, 37, 56, 69

[56] References Cited

U.S. PATENT DOCUMENTS 4,599,311  7/1986  Kawasaki ............ 435/6 X

FOREIGN PATENT DOCUMENTS

| | | | |
|---|---|---|---|
| 895961 | 6/1983 | Belgium .................. | 435/68 |
| 0042246 | 12/1981 | European Pat. Off. ....... | 435/172.3 |
| 114777 | 8/1984 | European Pat. Off. ....... | 435/68 |
| 0120551 | 10/1984 | European Pat. Off. ....... | 435/68 |
| 137633 | 4/1985 | European Pat. Off. ....... | 435/68 |
| 59-210888 | 11/1984 | Japan .................. | 435/68 |

OTHER PUBLICATIONS

Kurachi et al, *Proc. Natl. Acad. Sci.*, vol. 78, No. 11, Nov. 30, 1981, "Cloning and Sequence of a cDNA Encoding for α-1-Antitrypsin".

Chandra et al, *Biochem. Biophys. Res. Comm.*, vol. 103 (2), Nov. 30, 1981, "Induction of α-1-Antitrypsin mRNA and Cloning of its cDNA".

Woo et al, *Miami Winter Symp.*, vol. 19, from Jan. 1982, p. 579, Gene to Protein: Translation into Biotechnology.

Schochat et al, *J. Biol. Chem.*, vol. 253 (16), Aug. 25, 1975, pp. 5630–5634, "Primary Structure of Human α-1-Protease Inhibitor".

Hitzeman et al, *Nature*, vol. 293, Oct. 29, 1981, pp. 717–723, "Expression of a Human Gene for Interferon in Yeast".

Alber et al, *J. Mol. Appl. Genet.*, vol. 1, pp. 419–434, 1982, "Nucleotide Sequence of the Triose Phosphate Isomerase Gene of *Saccharomyces cerevisiae*".

Beggs, *Nature*, vol. 275, pp. 104–109, Sep. 14, 1978, "Transformation of Yeast by a Replicarry Hybrid Plasmid".

Broach et al, *Gene*, vol. 8, pp. 121–133, 1979.

Urdea et al., "Chemical Synthesis of a Gene for Human Epidermal Growth Factor Urogastrone and Its Expression in Yeast", *Proc. Natl. Acad. Sci.*, USA, vol. 80, pp. 7461–7465 (Dec. 1983).

Holland et al., "The Primary Structures of Two Yeast Enolase Genes", *J. Biol. Chem.*, vol. 256, pp. 1385–1395 (1981).

Holland et al., "Structural Comparison of Two Nontandenity Repeated Yeast Glyceraldehyde-3-Phosphate Dehydrogenase Genes", *J. Biol. Chem.*, vol. 255, No. 6, pp. 2596–2605 (Mar. 1980).

Kelly et al., "Effect of Transfer RNA from Various Sources on Placental Messenger RNA Translation", *Mol. Cell. Endocrin.*, 29, 181–195 (1983).

Ukemura, "Correlation Between the Abundance of Yeast Transfer RNAs and the Occurrence of Respective Codons in Protein Genes", *J. Mol. Biol.*, 158, 573–597 (1982).

Rogers et al., "The Isolation of a Clone for Human Alpha-1-Antitrypsin and the Detection of Alpha-1-Antitrypsin in mRNA from Liver and Leukocytes", *Biochem. Biophys. Res. Comm.*, 16: 375–382 (1983).

Valenzuela et al., *Nature*, vol. 298, 22 Jul. 1982, "Synthesis and Assembly of Hepatitis B Surface Antigen Particles in Yeast" pp. 347–350.

Ammerer et al, *Recombinant DNA Proc. 3rd Cleveland Symp. Micromol.*, ed. Walton, pp. 185–197, 1981.

Clifton et al., *Biochemistry*, 21 (8), Apr. 13, 1982, pp. 1935–1942.

Kawasaki et al., *Biochem. and Biophys. Res. Comm.*, 108 (3), Oct. 15, 1982, pp. 1107–1112.

Carlson et al., *FEBS Letters*, 130 (2), Aug. 1981, pp. 297–300.

Leicht et al., *Nature*, 297, Jun. 24, 1982, pp. 655–659.

*Primary Examiner*—Thomas G. Wiseman
*Assistant Examiner*—Robin Teskin
*Attorney, Agent, or Firm*—Flehr, Hohbach, Test, Albritton & Herbert

[57] ABSTRACT

A method is provided for expressing human alpha-1-antitrypsin in yeast utilizing a wild-type strain and a hyperproduction mutant, GK100.

5 Claims, 9 Drawing Sheets

FIG.1A

```
                                          5' GGGGGGGGGGGGGG CA CCA CCA CTG ACC
                                                            10             20

-24              -20                                               -10
              Met Pro Ser Ser Val Ser Trp Gly Ile Leu Leu Leu Ala Gly Leu
TGG GAC AGT GAA TCG ACA ATG CCG TCT TCT GTC TCG TGG GGC ATC CTC CTG CTG GCA GGC CTG
 30          40          50          60          70          80          90

-1  +1                                    10
Cys Cys Leu Val Pro Val Ser Leu Ala Glu Asp Pro Gln Gly Asp Ala Ala Gln Lys Thr Asp
TGC TGC CTG GTC CCT GTC TCC CTG GCT GAG GAT CCC CAG GGA GAT GCT GCC CAG AAG ACA GAT
         100         110         120         130         140         150

20                                  30
Thr Ser His His Asp Gln Asp His Pro Thr Phe Asn Lys Ile Thr Pro Asn Leu Ala Glu Phe
ACA TCC CAC CAT GAT CAG GAT CAC CCA ACC TTC AAC AAG ATC ACC CCC AAC CTG GCT GAG TTC
         160         170         180         190         200         210

40                                  50
Ala Phe Ser Leu Tyr Arg Gln Leu Ala His Gln Ser Asn Ser Thr Asn Ile Phe Phe Ser Pro
GCC TTC AGC CTA TAC CGC CAG CTG GCA CAC CAG TCC AAC AGC ACC AAT ATC TTC TTC TCC CCA
         220         230         240         250         260         270         280

60                                  70
Val Ser Ile Ala Thr Ala Phe Ala Met Leu Ser Leu Gly Thr Lys Ala Asp Thr His Asp Glu
GTG AGC ATC GCT ACA GCC TTT GCA ATG CTC TCC CTG GGG ACC AAG GCT GAC ACT CAC GAT GAA
              290         300         310         320         330         340

80                                  90
Ile Leu Glu Gly Leu Asn Phe Asn Leu Thr Glu Ile Pro Glu Ala Gln Ile His Glu Gly Phe
ATC CTG GAG GGC CTG AAT TTC AAC CTC ACG GAG ATT CCG GAG GCT CAG ATC CAT GAA GGC TTC
         350         360         370         380         390         400

100                                110
Gln Glu Leu Leu Arg Thr Leu Asn Gln Pro Asp Ser Gln Leu Gln Leu Thr Thr Gly Asn Gly
CAG GAA CTC CTC CGT ACC CTC AAC CAG CCA GAC AGC CAG CTC CAG CTG ACC ACC GGC AAT GGC
         410         420         430         440         450         460         470

120                                130
Leu Phe Leu Ser Glu Gly Leu Lys Leu Val Asp Lys Phe Leu Glu Asp Val Lys Lys Leu Tyr
CTG TTC CTC AGC GAG GGC CTG AAG CTA GTG GAT AAG TTT TTG GAG GAT GTT AAA AAG TTG TAC
              480         490         500         510         520         530

140                                150
His Ser Glu Ala Phe Thr Val Asn Phe Gly Asp Thr Glu Glu Ala Lys Lys Gln Ile Asn Asp
CAC TCA GAA GCC TTC ACT GTC AAC TTC GGG GAC ACC GAA GAG GCC AAG AAA CAG ATC AAC GAT
         540         550         560         570         580         590

160                                     170                                      180
Tyr Val Glu Lys Gly Thr Gln Gly Lys Ile Val Asp Leu Val Lys Glu Leu Asp Arg Asp Thr
TAC GTG GAG AAG GGT ACT CAA GGG AAA ATT GTG GAT TTG GTC AAG GAG CTT GAC AGA GAC ACA
    600         610         620         630         640         650

190                                      200
Val Phe Ala Leu Val Asn Tyr Ile Phe Phe Lys Gly Lys Trp Glu Arg Pro Phe Glu Val Lys
GTT TTT GCT CTG GTG AAT TAC ATC TTC TTT AAA GGC AAA TGG GAG AGA CCC TTT GAA CTC AAG
660         670         680         690         700         710         720

210                                220
Asp Thr Glu Glu Glu Asp Phe His Val Asp Gln Val Thr Thr Val Lys Val Pro Met Met Lys
GAC ACC GAG GAA GAG GAC TTC CAC GTG GAC CAG GTG ACC ACC GTG AAG GTG CCT ATG ATG AAG
         730         740         750         760         770         780

230                                240
Arg Leu Gly Met Phe Asn Ile Gln His Cys Lys Lys Leu Ser Ser Trp Val Leu Leu Met Lys
CGT TTA GGC ATG TTT AAC ATC CAG CAC TGT AAG AAG CTG TCC AGC TGG GTG CTG CTG ATG AAA
         790         800         810         820         830         840
```

```
                              250                                              260
Tyr Leu Gly Asn Ala Thr Ala Ile Phe Phe Leu Pro Asp Glu Gly Lys Leu Gln His Leu Glu
TAC CTG GGC AAT GCC ACC GCC ATC TTC TTC CTG CCT GAT GAG GGG AAA CTA CAG CAC CTG GAA
850             860         870         880         890         900         910

270                                        280
Asn Glu Leu Thr His Asp Ile Ile Thr Lys Phe Leu Glu Asn Glu Asp Arg Arg Ser Ala Ser
AAT GAA CTC ACC CAC GAT ATC ATC ACC AAG TTC CTG GAA AAT GAA GAC AGA AGG TCT GCC AGC
        920         930         940         950         960         970

290                                            300
Leu His Leu Pro Lys Leu Ser Ile Thr Gly Thr Tyr Asp Leu Lys Ser Val Leu Gly Gln Leu
TTA CAT TTA CCC AAA CTG TCC ATT ACT GGA ACC TAT GAT CTG AAG AGC GTC CTG GGT CAA CTG
            980         990         1000        1010        1020        1030

310                                            320
Gly Ile Thr Lys Val Phe Ser Asn Gly Ala Asp Leu Ser Gly Val Thr Glu Glu Ala Pro Leu
GGC ATC ACT AAG GTC TTC AGC AAT GGG GCT GAC CTC TCC GGG GTC ACA GAG GAG GCA CCC CTG
    1040        1050        1060        1070        1080        1090        1100

330                                            350
Lys Leu Ser Lys Ala Val His Lys Ala Val Leu Thr Ile Asp Glu Lys Gly Thr Glu Ala Ala
AAG CTC TCC AAG GCC GTG CAT AAG GCT GTG CTG ACC ATC GAC GAG AAA GGG ACT GAA GCT GCT
        1110        1120        1130        1140        1150        1160

Gly Ala Met Phe Leu Glu Ala Ile Pro Met Ser Ile Pro Pro Glu Val Lys Phe Asn Lys Pro
GGG GCC ATG TTT TTA GAG GCC ATA CCC ATG TCT ATC CCC CCC GAG GTC AAG TTC AAC AAA CCC
        1170        1180        1190        1200        1210        1220

380                                    390
Phe Val Phe Leu Met Ile Glu Gln Asn Thr Lys Ser Pro Leu Phe Met Gly Lys Val Val Asn
TTT GTC TTC TTA ATG ATT GAA CAA AAT ACC AAG TCT CCC CTC TTC ATG GGA AAA GTG GTG AAT
    1230        1240        1250        1260        1270        1280

394
  Pro Thr Gln Lys STOP
  CCC ACC CAA AAA TAA CTG CCT CTC GCT CCT CAA CCC CTC CCC TCC ATC CCT GGC CCC CTC CCT
1290        1300        1310        1320        1330        1340        1350

GGA TGA CAT TAA AGA AGG GTT GAG CTG
        1360        1370

G AAAAAAAAAAAAAAAA CCCCCCCCCCCCCCCCCCCCCCCCCCCCCCCCCCCCCCC  3'
1380        1390        1400        1410        1420        1430
```

5' CCCCCCCCCCCCCCCAGTGAATCGACA

```
-24                 -20                                              -10
Met Pro Ser Ser Val Ser Trp Gly Ile Leu Leu Leu Ala Gly Leu
ATG CCC TCT TCT GTC TCG TGG GGC ATC CTC CTG CTG GCA CGC CTG
+1          10          20              30              40

+1                                   -1   1
Cys Cys Leu Val Pro Val Ser Leu Ala Glu Asp Pro Gln Gly Asp
TGC TGC CTG GTC CCT GTC TCC CTG GGT GAC GAT CCG CAG GGA GAT
50              60              70              80              90

10                                  20
Ala Ala Gln Lys Thr Asp Thr Ser His His Asp Gln Asp His Pro
GCT GCC CAC AAG ACA GAT ACA TCC CAC CAT GAT CAG GAT CAC CCA
            100             110             120             130

30
Thr Phe Asn Lys Ile Thr Pro Asn Leu Ala Glu Phe Ala Phe Ser
ACC TTC AAC AAG ATC ACC CCC AAC TTG GGT GAC TTG GCC TTC AGC
        140             150             160         170             180

40                                          50
Leu Tyr Arg Gln Leu Ala His Gln Ser Asn Ser Thr Asn Ile Phe
CTA TAC GGC CAG GTG CCA CAC CAG TCC AAC AGC ACC AAT ATC ITC
            190             200             210             220

60
Phe Ser Pro Val Ser Ile Ala Thr Ala Phe Ala Met Leu Ser Leu
TTC TCC GGA GTG AGC ATC CCT ACA GCC TTT CCA ATG CTC TCC CTG
    230             240             250             260             270

70                                          80
Gly Thr Lys Ala Asp Thr His Asp Glu Ile Leu Glu Gly Leu Asn
CGG ACC AAG GCT CAC ACT CAC GAT GAA ATC CTG GAG GGC CTG AAT
            280             290             300             310

90
Phe Asn Leu Thr Glu Ile Pro Glu Ala Gln Ile His Glu Gly Phe
ITC AAC CTC ACG GAG ATT CCG GAC CCT CAC ATC CAT GAA CCC TTC
    320             330             340             350             360

100                                         110
Gln Glu Leu Leu Arg Thr Leu Asn Gln Pro Asp Ser Gln Leu Gln
CAG GAA CTC CTC CCT ACC CTC AAC CAG CCA GAC AGC CAG CTC CAG
            370             380             390             400

120
Leu Thr Thr Gly Asn Gly Leu Phe Leu Ser Glu Gly Leu Lys Leu
CTG ACC ACC CCC AAT GGC GTG TTC CTC AGC CAG GCC CTG AAC CTA
    410             420             430             440             450

130                                         140
Val Asp Lys Phe Leu Glu Asp Val Lys Lys Leu Tyr His Ser Glu
GTG CAT AAG TTT ITG GAG GAT CTT AAA AAG TTG TAC CAC TCA GAA
            460             470             480             490
```

FIG. 1B CONT.

```
                                        150
Ala Phe Thr Val Asn Phe Gly Asp Thr Glu Glu Ala Lys Lys Gln
GCC TTC ACT GTC AAC TTC GGG GAC ACC GAA GAG CCC AAG AAA CAG
    500         510         520         530         540
                160                                 170
Ile Asn Asp Tyr Val Glu Lys Gly Thr Gln Gly Lys Ile Val Asp
ATC AAC GAT TAC GTG CAG AAG GGT ACT CAA CGC AAA ATT CTG GAT
            550         560         570         580
                                180
Leu Val Lys Glu Leu Asp Arg Asp Thr Val Phe Ala Leu Val Asn
TTG GTC AAC CAC CTT GAC AGA GAC ACA GTT TTT CCT CTC CTG AAT
    590         600         610         620         630
                190                                 200
Tyr Ile Phe Phe Lys Gly Lys Trp Glu Arg Pro Phe Glu Val Lys
TAC ATC TTC TTT AAA GGC AAA TGG GAC ACA CCC TTT GAA CTC AAG
            640         650         660         670
                                210
Asp Thr Glu Glu Glu Asp Phe His Val Asp Gln Val Thr Thr Val
GAC ACC GAG GAA GAG GAC TTC CAC CTG GAC CAG GTG ACC ACC GTG
    680         690         700         710         720
                220                                 230
Lys Val Pro Met Met Lys Arg Leu Gly Met Phe Asn Ile Gln His
AAG CTC CCT ATG ATG AAG CCT TTA CCC ATC TTT AAC ATC CAG CAT
            730         740         750         760
                                240
Cys Lys Lys Leu Ser Ser Trp Val Leu Leu Met Lys Tyr Leu Gly
TGT AAG AAG CTG TCC ACC TCC GTG CTG CTG ATC AAA TAC CTG GGC
    770         780         790         800         810
                250                                 260
Asn Ala Thr Ala Ile Phe Phe Leu Pro Asp Glu Gly Lys Leu Gln
AAT GCC ACC GCC ATC TTC TTC CTG CCT GAT GAG GGG AAA CTA CAC
            820         830         840         850
                                270
His Leu Glu Asn Glu Leu Thr His Asp Ile Ile Thr Lys Phe Leu
CAC CTG GAA AAT GAA CTC ACC CAC GAT ATC ATC ACC AAG TTC CTC
    860         870         880         890         900
                280                                 290
Glu Asn Glu Asp Arg Arg Ser Ala Ser Leu His Leu Pro Lys Leu
GAA AAT GAA CAC AGA AGC TCT CCC AGC TTA CAT TTA CCC AAA CTG
            910         920         930         940
                                300
Ser Ile Thr Gly Thr Tyr Asp Leu Lys Ser Val Leu Gly Gln Leu
TCC ATT ACT GGA ACC TAT GAT GTG AAG AGC CTC CTA CGT CAA CTG
    950         960         970         980         990
                310                                 320
Gly Ile Thr Lys Val Phe Ser Asn Gly Ala Asp Leu Ser Gly Val
GGG ATC ACT AAG GTC TTC ACC AAT GCC GCT GAC CIC TCC CGG GTC
            1000        1010        1020        1030
```

```
                                        330
Thr Glu Glu Ala Pro Leu Lys Leu Ser Lys Ala Val His Lys Ala
ACA GAG GAC CCA CCC CTG AAG GTC TCC AAC CCC CTG CAT AAG CCT
  1040        1050        1060        1070        1080
                340
Val Leu Thr Ile Asp Glu Lys Gly Thr Glu Ala Ala Gly Ala Met
GTG CTG ACC ATC GAC GAG AAA GGG ACT GAA GCT GCT GGG CCC ATG
   1090        1100        1110        1120
                                360
Phe Leu Glu Ala Ile Pro Met Ser Ile Arg Pro Glu Val Lys Phe
TTT TTA GAG GCC ATA CCC ATC TCT ATC CGC CCC CAG GTC AAG TTC
  1130        1140        1150        1160        1170
         370                                 380
Asn Lys Pro Phe Val Phe Leu Met Ile Glu Gln Asn Thr Lys Ser
AAC AAA CCC TTT GTC TTC TTA ATG ATT GAA CAA AAT ACC AAG TCT
         1180        1190        1200        1220
                                390        394
Pro Leu Phe Met Gly Lys Val Val Asn Pro Thr Gln Lys STOP
CCC CTC TTC ATG GGA AAA GTG GTG AAT CCC ACC CAA AAA TAA
  1220        1230        1240        1250

CTGCCTCTCGCTCCTCAACCCCCCCCCC₃,
```

FIG.1B CONT.

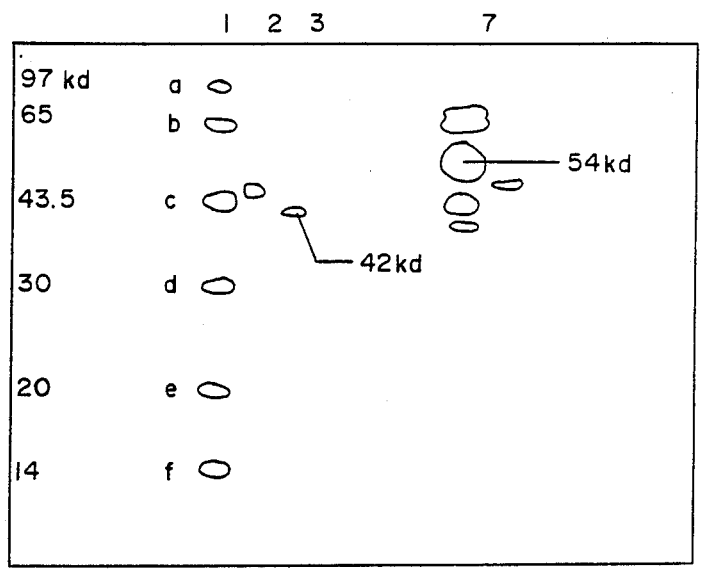
FIG. —3
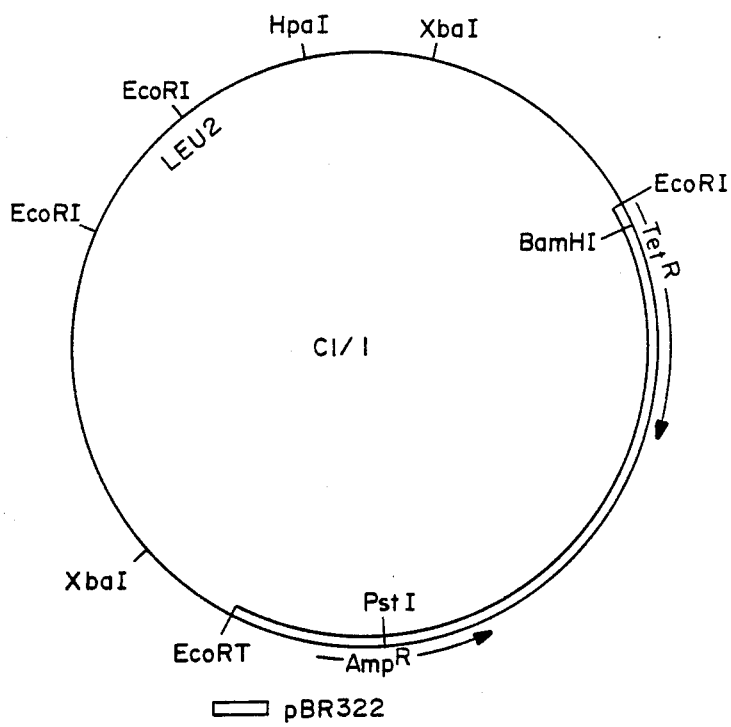
FIG. —4

```
              1   2   3   4  PRO SER LEU GLY CYS ARG SER THR LEU GLU ASP PRO ARG ALA SER SER
M13mpII/pUCI3  THR MET ILE THR                                                            ASN SER LEU ALA
              1   2   3   4   1   2   3   4   5   6   7   8   9  10  11  12  13  14  15  16
                                                                                           5   6   7   8
ATG ACC ATG ATT ACG CCA AGC TTG GGC TGC AGG TCG ACT CTA GAG GAT CCC CGG GCG AGC TCG AAT TCA CTG GCC
            HindIII     PstI    SalI    XbaI    BamHI    XmaI   SstI   EcoRI        HaeIII
                                AccI,HincII              SmaI
```

FIG.—5

METHOD OF EXPRESSING ALPHA-1-ANTITRYPSIN IN YEAST

This application is related to Ser. No. 408,099, filed Aug. 13, 1982, now allowed U.S. Pat. No. 4,599,311 the disclosure of which is incorporated herein by reference in its entirety.

The present invention is directed to a method of expressing human alpha-1-antitrypsin in yeast and to the protein product expressed thereby.

Alpha-1-antitrypsin is a protease inhibitor present in mammalian blood whose apparently major physiological function is to inhibit elastase, a potent protease which hydrolyzes structural proteins. Alpha-1-antitrypsin also inhibits other serine proteases. The normal plasma level of alpha-1-antitrypsin is about 2 mg/ml. A low level of alpha-1-antitrypsin in the blood may be associated with chronic obstructive pulmonary emphysema and infantile liver cirrhosis. Under many inflammatory conditions, an acute-phase response is initiated and the concentration of alpha-1-antitrypsion is substantially increased. In order to study and treat alpha-1-antitrypsin deficiency and to examine the mechanism of the acute-phase response, it is therefore desirable to have a pure alpha-1-antitrypsin protein. In particular, it is desirable to have a source of antitrypsin protein produced by microorganisms through genetic engineering techniques.

It is therefore an object of the present invention to provide a method for producing alpha-1-antitrypsin in microorganisms, preferably in yeast.

It is a further object of the present invention to provide a pure alpha-1-antitrypsin polypeptide which has been profuced by genetic engineering techniques.

BRIEF DESCRIPTION OF THE FIGURES

In the accompanying FIGURES:

FIG. 1 is the cDNA sequence of the gene coding the predominant form of human alpha-1-antitrypsin.

FIG. 3 is a diagram of the electrophoresis chromatogram showing purified alpha-1-antitrypsin produced according to the present invention.

FIG. 4 illustrates the restriction map of plasmid C1/1.

FIG. 5 illustrates the DNA sequence of the multiple restriction site of pUC13.

The sequencing of chromosomal DNA coding for alpha antitrypsin has been described by Kurachi et al., *Proc. Natl. Acad. Sci. U.S.A.*, 78, 6826–6830 (1981) and by Chandra et al., *Biochem. Biophys. Res. Comm.*, 103, 751–758 (1981), the disclosures of which are incorporated herein by reference. A primate gene for alpha-1-antitrypsin may be obtained by DNA cloning methods described by Chandra et al., ibid. The gene coding for the predominant form of human alpha-1-antitrypsin, isolated from a human cDNA library by using the baboon sequence as a DNA hybridization probe is shown in FIG. 1.

Figure 2:
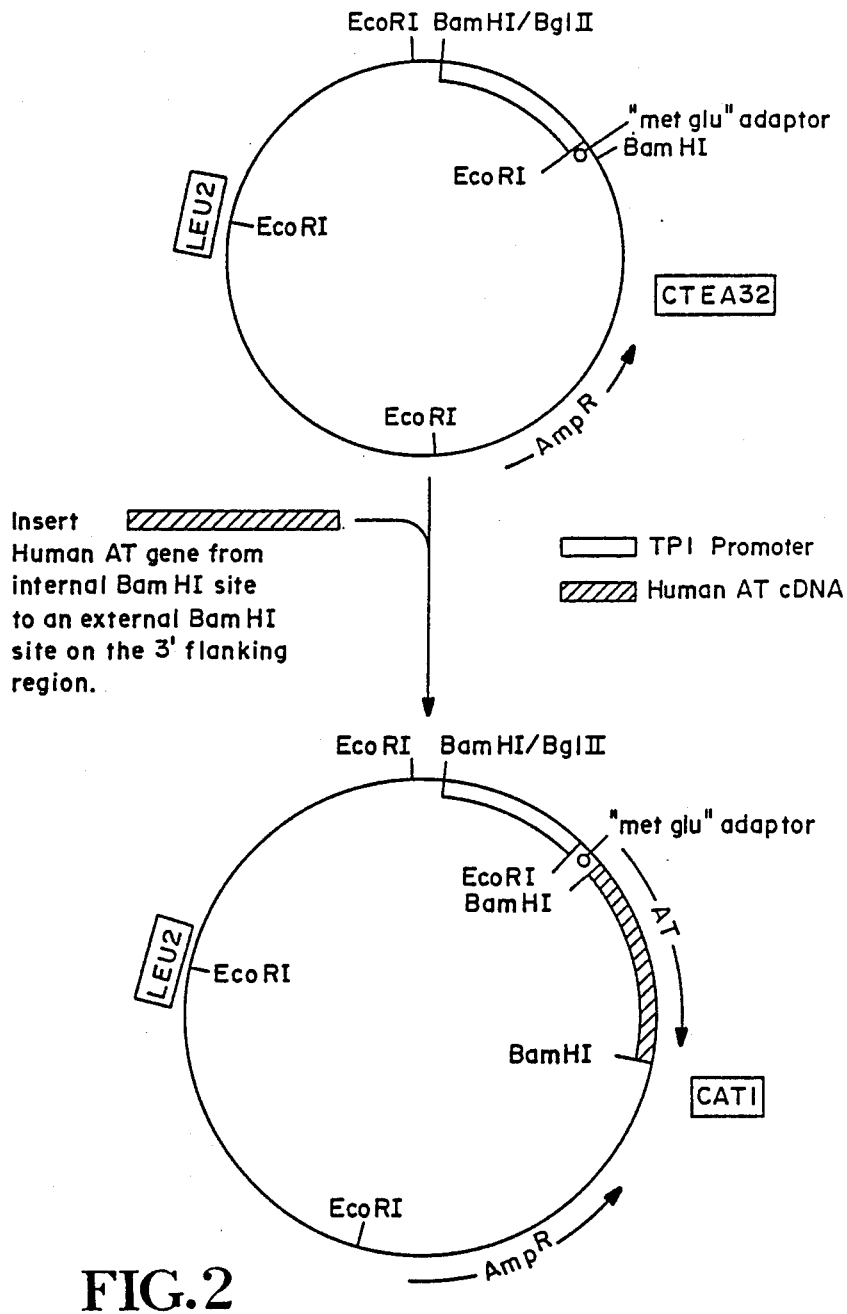
FIG. 2 illustrates the restriction maps of plasmids CTEA32 and CAT1.

The cDNA coding for alpha-1-antitrypsin (hereinafter "AT") may then be inserted into an expression vector, such as CTEA32 (FIG. 2), which contains the yeast promoter for triose phosphate isomerase (TPI) inserted at the BamHI site of the shuttle plasmid, CV13 [Broach J. R., Strathern J. N., Hicks J. B., *Gene*, 8:121–133 (1979)]. A synthetic DNA adaptor was ligated into the TPI promoter after the TPI structural sequences were removed by BAL31 digestion from the KpnI restriction site within the TPI coding region. (Alber et al, *J. Molec. Applied Genet.*, 1, 419–434 (1982)). This adaptor contained an ATG codon for translation initiation, followed by the sequence GAGGATCC. The GAG codon specifies a glutamic acid residue, which is the first amino acid of the naturally-occurring human AT. The GGATCC portion of the adaptor is a cutting site for BamHI endonuclease and allows for the splicing of the remainder of human AT DNA sequence into this vector. The BamHI site of CTEA32 was constructed to be "in frame" with the rest of the AT structural gene, thereby allowing for the expression of the polypeptide when a BamHI fragment from the cloned cDNA is appropriately inserted into CTEA32. The plasmid consisting of CTEA32 plus the AT gene is called CAT1 (FIG. 2).

This DNA construct containing the gene for human AT located downstream to a yeast triose phosphate isomerase (TPI) promoter fragment was transformed into yeast strains, N501-B and GK100. Transformation into yeast is described by Beggs, *Nature* 275, 104–109 (1978). Screening of the transformed yeast strains by immunological assays (competition assays and ELISA assays, using antibodies against alpha-1-antitrypsin) confirmed the presence of large amounts of human AT in yeast made from the plasmid CAT1. The "wild-type" yeast strain, N501-1B (described by Kawasaki et al., *Biochem. Biophys. Res. Comm.*, 108, 1107–1112 (1982)), when transformed with CAT1, produced 1.8 mg alpha-1-antitrypsin per gram of soluble protein (or 0.18% alpha-1-antitrypsin), when grown at 30° on a synthetic minimal medium (modified Wickerham's medium) with 6% glucose. A mutant yeast strain, GK100, when transformed with CAT1, produced 10–15 mg alpha-1-antitrypsin per gram soluble protein (or 1–1.5% alpha-1-antitrypsin) under the same growth conditions. Strains N501-1B and GK100 each carry a defective LEU2 gene which allows for the selective maintenance on minimal and leucine-less media of CV13 and CV13-derived plasmids (such as CAT1) which each contain a functional LEU2 gene. When grown on minimal media with only CV13 as a control, N501-1B and GK100 produce no detectable AT. Thus, AT may be specifically produced by the CAT1 plasmid.

Since GK100 produces significantly more AT than N501-1B, it is preferred. However, the present invention is not limited to AT production by GK100. It may be desirable to utilize mutations in GK100 which lead to hyperproduction of AT.

An immuno-adsorption column, made according to the method of Cuatrecasas, P. *J. Biol. Chem.*, 245, 3059 (1970), was prepared by covalently attaching affinitypurified goat antibodies to human AT to CNBr-activated Sepharose. Disrupted GK100 yeast cells were extracted with 3 volumes of phosphate buffered saline pH 7.2 containing 0.5M NaCl, and the extracts were applied to the column. Yeast produced human AT (0.5–1.0 mg) was eluted from the column with 3M NaSCN. After the material was dialyzed to remove salt it was analyzed by electrophoresis on a polyacrylamide gel in the presence of sodium dodecyl sulfate, the results of which are shown in FIG. 3. Based on the relative migration of the protein in the gel, the approximate molecular weight of the human alpha-1-antitrypsin made in yeast is 42,000–43,000 daltons. Naturally occurring human AT has a molecular weight of approximately 54,000 daltons, having a carbohydrate composition of approximately 16% by weight, as shown by Hodges et al, *J. Biol. Chem.*, 254, 8208–8212 (1979). It therefore appears that the yeast produced AT may be unglycosylated or substantially unglycosylated and may lack carbohydrate portions present in the naturally occurring protein.

Alternatively, other expression vectors may be constructed which contain a segment coding for alpha-1-antitrypsin. Such expression vectors may be constructed by methods known to those of ordinary skill in the art using available DNA constructs. A preferred vector is plasmid C1/1, which is more stable than CV13 and CV13 derived vectors, such as CAT1. C1/1 was constructed from plasmid, pJDB248 (Beggs, J., *Nature* 275, 104–109 (1978)). The pMB9 sequences were removed from pJDB248 by partial digestion with Eco RI and were replaced by pBR322 DNA which was cut with Eco RI. The restriction map of C1/1 is given in FIG. 4. The C1/1 plasmid contains the entire 2-micron DNA from yeast (*S.cervisiae*), with a pBR322 insertion at an EcoRI site. It also contains the LEU2 gene. Thus, the yeast TPI promotor with the adaptor may be inserted into the single BamHI site in the Tc$^R$ gene of C1/1. Then the AT sequence, attached to a transcription terminator fragment from the yeast TPI gene, may be inserted into the BamHI side downstream from the TPI promotor. The resulting plasmid, HAT4, may then be transformed into N501-1B and GK100 in a manner as described above.

The sequence of the first ten amino acids in the yeast-produced AT may be confirmed by amino acid sequence analysis as identical to the first ten amino acids of the naturally occurring human AT:

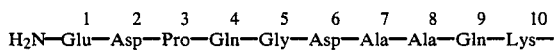

The yeast-produced AT does not contain the initiation methionine which is specified by the ATG start codon.

The polypeptides produced according to the present invention having AT activity may be useful for treatment of a genetic AT deficiency and other diseased states related to inadequate levels of AT. Thus, conditions such as emphysema and other lung disorders related to progressive digestion of lung sacs may be treated, such as, chronic obstructive pulmonary disease or adult respiratory distress syndrome. Non-genetically related emphysema may also be treated, such as, emphysema resulting from heavy smoking. Conditions not necessarily confined to the lungs may also be treated, such as, cystic fibrosis and arthritis. For a review of AT deficiency, see Gadek, J. E., and R. Crystal, "α1-Antitrypsin Deficiency", *The Metabolic Basis of Inherited Disease*, J. B. Stanbury, J. B. Wyngaarden, D. S. Fredrickson, McGraw-Hill, N.Y. pp. 1450-67 (1982).

The polypeptides according to the present invention may be admixed with conventional pharmaceutical carriers. Preferably, the polypeptides are to be administered intravenously or by inhalation. While the effective dosages may vary according to the severity of the condition and weight of the subject, dosages in the range of 0.5–10.0 gm/week of a polypeptide introduced intravenously may, in many cases, be effective. Lower dosages may be effective if the method of administration is by inhalation. Oral administration may also be effective provided the AT is protected in capsules or coated carriers from premature degradation in the digestive tract.

The following examples set forth specific embodiments according to the present invention, but the invention is not intended to be limited thereto.

EXAMPLE 1

Purification Of Alpha-1-Antitrypsin From Yeast GK100 Yeast Extracts

An immuno adsorption column was prepared by covalently attaching affinity-purified antibodies to human alpha-1-antitrypsin to CNBr-activated Sepharose according to the method of Cuatrecasas, *J. Biol. Chem.*, 245, 3059 (1970). Disrupted GK100 cells were extracted with three volumes of phosphate buffered saline pH 7.2 containing 0.5M NaCl and applied to the column. The column was eluted with 3M NaSCN and the recovered material was analyzed by electrophoresis on polyacrylamide gel in the presence of sodium dodecyl sulfate. The results of the electrophoresis are shown in FIG. 3. Track 1 contained a mixture of molecular weight standards: (a) phosphorylase B, 97,000 daltons; (b) bovine serum albumen (BSA), 65,000 daltons; (c) ovalbumin, 43,500 daltons; (d) carbonic anhydrase, 30,000 daltons; (e) soybean trypsin inhibitor, 20,000 daltons; and (f) alpha-lactalbumin, 14,000 daltons. Track 3 contains yeast produced AT purified by immunoadsorption, molecular weight about 42,000 daltons. Track 7 is a sample of naturally occurring AT purchased from Sigma Chemical Company, heavily contaminated by blood proteins. A major component of Track 7 is human alpha-1-antitrypsin, molecular weight 54,000 daltons.

EXAMPLE 2

Activity Of Yeast Produced Alpha-1-Antitrypsin Against Serine Protease Trypsin

As a control, 10 microliters (1 microgram) of a solution of 100 microgram/ml trypsin, 100 microgram (100 microliters) of bovine serum albumin and 100 microliters of 0.05 molar TRIS, pH 8.0 buffer containing 1 mM benzoylarginioyl-p-nitroanilide were mixed, and the increase in absorbance at 405 nm was measured over time in a spectrophotometer. The absorbance value of this solution was used as a standard for 100% trypsin activity. Three additional samples were run in duplicate, each containing 1 μl trypsin and, respectively containing 25 μl AT solution plus 175 μl buffer, 100 μl alpha-1-antitrypsin plus 100 μl buffer, and 200 μl alpha-1-antitrypsin. All samples contain equal concentrations of substrate and bovine serum albumin. The results demonstrated that utilizing 25 microliters of AT, 73% of the trypsin activity remained, with 100 microliters of AT, 41% of trypsin activity remained and with 200 microliters of alpha-1-antitrypsin, 26% of the trypsin activity remained. This demonstrated that by increasing the levels of the yeast made AT the trypsin inhibitory activity also increased.

EXAMPLE 3

Production of Alpha-1-Antitrypsin From Yeast Plasmids With Increased Genetic Stability Increased levels of AT may be obtained by utilizing C1/1, a plasmid which is more genetically stable than CV13. The C1/1 plasmid contains the entire 2-micron DNA from *S. cerevisiae* and, therefore, can promote its own replication and maintenance in yeast in the absence of selection for a genetic marker. Also, C1/1 plasmid has a single BamHI site located in the Tc$^R$ gene. Transformants carrying C1/1 may be selected in *E. coli* by ampicillin- or tetracycline-resistance and in yeast by leucine prototrophy. C1/1 contains pBR322 inserted into an EcoRI site of 2-micron DNA and carries the LEU2 gene described by J. Beggs, *Nature,* 275, 104–109 (1978).

The yeast TPI promoter (from CTEA32) with the synthetic DNA adaptor (described above) was inserted as a Bgl II BamHI fragment (about 900 base pairs) into the BamHI site of C1/1. This insertion created a single BamHI site into which the human AT gene could be spliced for expression in yeast. As in the CAT1 plasmid, when the AT gene (FIG. 1) is inserted, the resultant plasmid would have an ATG initiation codon followed by a GAG (glutamic acid codon) to allow the production of mature human AT protein sequence in yeast.

About 700 base pairs of the 3' flanking region of the yeast TPI gene was added after the human AT sequence to assist in transcription termination. The "termination" fragments are sequences from the XbaI to EcoRI sites in the plasmid TPIC10 (T. Alber and G. Kawasaki, *J. Molec. Applied Genet.,* 1, 419–434 (1982)).

Figure 6:
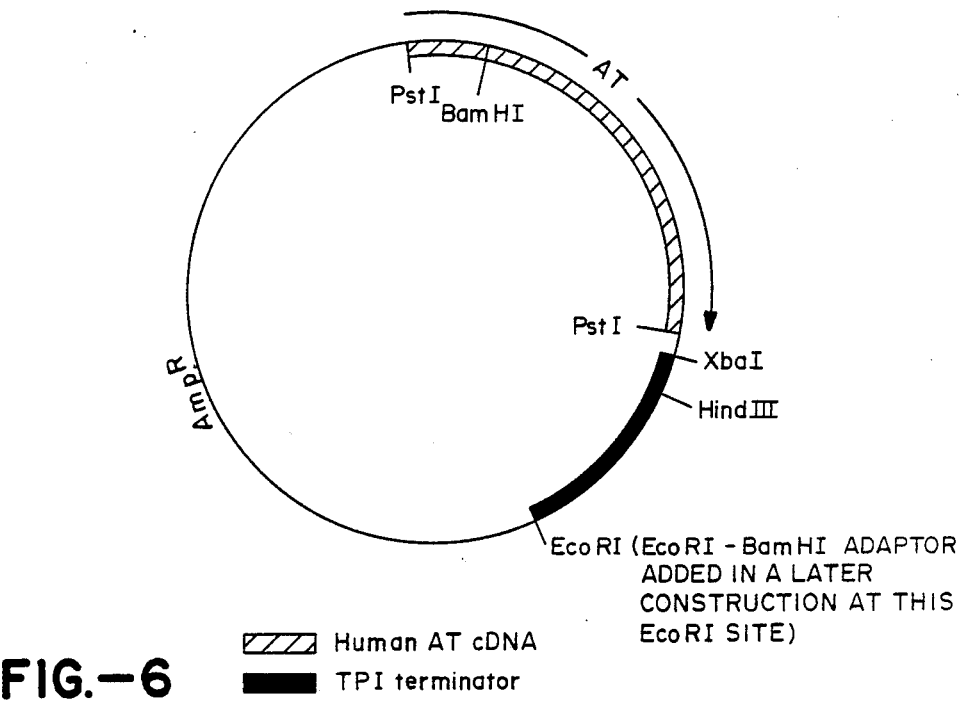
FIG. 6 illustrates the restriction map of plasmid pUCα1 containing the DNA sequence from FIG. 1.

The yeast termination sequences were attached to the human AT gene by using the vector, pUC13, which has multiple cloning sites into which the terminator and AT DNA's can be separately inserted. The pUC13 plasmid was constructed as described in Vieira, J., and Messing; J., Gene 19, 259–268 (1982) for vectors, pUC8 and pUC9. The pUC13 plasmid contained the multiple restriction site, depicted in FIG. 5, at the start of the lac Z gene. To connect the human AT gene to the TPI transcription terminator, the AT cDNA clone (FIG. 1) was inserted as a Pst I fragment into pUC13 at the single Pst I site. The AT gene was followed by an Xba I site and Eco RI site in the multiple cloning sequence. Between these Xba I and Eco RI sites of pUC13 was inserted the yeast TPI terminator as a 700 base pair Xba I-Eco RI fragment from pTPIC10. The resulting plasmid, pUCα1+FG1, contained a human AT gene with a yeast transcription terminator (See FIG. 6). An Eco RI-Bam HI synthetic DNA adaptor was then added to the Eco RI site of the plasmid, in order to create a Bam HI site on the 5' end of the yeast terminator. By using this adaptor, the human AT-yeast terminator sequence could be removed by cutting with Bam HI to liberate a fragment of approximately 2100 base pairs. This BamHI fragment was inserted into the C1/1 plasmid containing the TPI promoter with BamHI adaptor.

Figure 7:
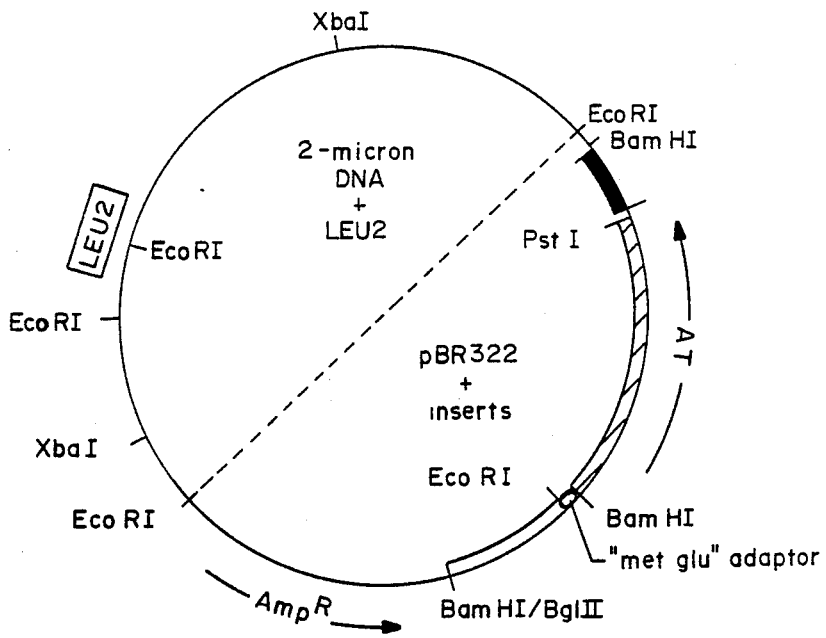
FIG. 7 is the restriction map of plasmid HAT4.

The resulting plasmid, HAT4, has the TPI promoter, ATGGAGGATCC adapter, human AT gene (from the BamHI site), and TPI terminator inserted into C1/1. The topology of HAT4 is depicted in FIG. 7.

HAT4 was transformed into N501-1B and GK100. On minimal media with 6% glucose, 2–3% of the yeast soluble protein was alpha-1-antitrypsin at a cell density of nearly 3 g per liter (wet weight). Because HAT4 contained C1/1, this plasmid was maintainable in a variety of rich media, including YEPD (1% yeast extract, 2% peptone, and 2% glucose). On rich media 2–3% AT was still produced but at a higher cell density of 10–20 g per liter (wet weight). The HAT4 plasmid was maintained without selection in N501-1B for over 30 divisions on rich media with greater than 70% of the cells containing the plasmid. In GK100 better than 95% of the cells had HAT4 after 30 divisions on rich media. The advantages of using HAT4 over CAT1 were (1) greater plasmid stability, (2) higher levels of AT as a percentage of total protein, (3) much greater yields of cells per liter as a result of using rich media, and (4) cheaper costs of rich media compared to synthetic (leucine-less) media. The mutant yeast strain GK100 has been placed on deposit in the American Type Culture Collection, Rockville, Maryland, ATCC No. 20669.

What is claimed is:

1. A method of producing a polypeptide having the protease inhibition activity of humane alpha-1-antitrypsin, comprising the steps of transforming a DNA transfer vector into a yeast culture comprising cells of the mutant strain GK-100 and growing said culture under conditions suitable for expression of said polypeptide, said vector comprising a segment coding for human alpha-1-antitrypsin and a promoter capable of controlling expression of said polypeptide in said yeast culture.

2. A method according to claim 1 wherein said vector comprises plasmid CAT1.

3. A method according to claim 1 wherein said vector comprises plasmid HAT4.

4. A DNA construct capable of expression in a microorganism of a polypeptide having the protease inhibition activity of human alpha-1-antitrypsin, said construct comprising plasmid HAT4.

5. A yeast transformant containing a DNA element comprising plasmid HAT4.

* * * * *

UNITED STATES PATENT AND TRADEMARK OFFICE
CERTIFICATE OF CORRECTION

PATENT NO. : 4,839,283

DATED : June 13, 1989

INVENTOR(S) : Glenn H. Kawasaki; Richard Woodbury

It is certified that error appears in the above-identified patent and that said Letters Patent is hereby corrected as shown below:

On the cover page, under the heading "Inventors:", please delete "Richard Woodbury, both of"

In column 1, line 22, delete "alpha-1-antitrypsion" and insert therefor --alpha-1-antitrypsin--.

In column 1, line 35, delete "profused" and substitute therefor --produced--.

In column 1, line 53, delete "alpha antitrypsin" and substitute therefor --alpha-1-antitrypsin--.

In column 3, line 23, delete "cervisiae" and insert therefor --cerevisiae--.

In column 3, line 45, delete "diseased" and insert therefor --disease--.

UNITED STATES PATENT AND TRADEMARK OFFICE
CERTIFICATE OF CORRECTION

PATENT NO. : 4,839,283

DATED : June 13, 1989

INVENTOR(S) : Glenn H. Kawasaki; Richard Woodbury

It is certified that error appears in the above-identified patent and that said Letters Patent is hereby corrected as shown below:

In column 4, line 21, following "on" insert --a--.

In column 4, line 52, delete "contain" and insert therefor
--contained--.

In column 5, line 13, delete "BgI II BamHI" and substitute therefor --BgI II-Bam HI--.

In claim 1, column 6, line 31, please delete "humane" and substitute therefor --human--.

Signed and Sealed this

Fifth Day of March, 1991

Attest:

HARRY F. MANBECK, JR.

*Attesting Officer*  *Commissioner of Patents and Trademarks*